United States Patent
Lowe et al.

(10) Patent No.: US 7,443,553 B2
(45) Date of Patent: Oct. 28, 2008

(54) HOLOGRAPHIC SENSORS AND THEIR PRODUCTION

(75) Inventors: Christopher Robin Lowe, Cambridge (GB); Colin Alexander Bennett Davidson, Cambridge (GB); Jeffrey Blyth, Cambridge (GB); Alexander James Marshall, Cambridge (GB); Anthony Peter James, Cambridge (GB)

(73) Assignee: Smart Holograms Limited, Cambridge (GB)

( * ) Notice: Subject to any disclaimer, the term of this patent is extended or adjusted under 35 U.S.C. 154(b) by 4 days.

(21) Appl. No.: 10/544,422

(22) PCT Filed: Mar. 11, 2004

(86) PCT No.: PCT/GB2004/000979

§ 371 (c)(1),
(2), (4) Date: Oct. 18, 2006

(87) PCT Pub. No.: WO2004/081546

PCT Pub. Date: Sep. 23, 2004

(65) Prior Publication Data

US 2007/0036674 A1  Feb. 15, 2007

(30) Foreign Application Priority Data

Mar. 11, 2003  (GB)  ................... 0305591.0

(51) Int. Cl.
*G03H 1/00* (2006.01)
*G03H 1/02* (2006.01)
*G02B 5/32* (2006.01)
*G01N 15/06* (2006.01)
*G01N 7/00* (2006.01)

(52) U.S. Cl. ........... 359/9; 359/1; 359/3; 359/15; 359/20; 359/22; 359/23; 359/24; 359/25; 422/50; 422/68.1; 422/83; 427/466; 427/468

(58) Field of Classification Search ............... 422/50, 422/68.1, 83; 427/466, 468; 359/1, 3, 9, 359/15, 20, 22, 23, 24, 25
See application file for complete search history.

(56) References Cited

U.S. PATENT DOCUMENTS

| | | | | |
|---|---|---|---|---|
| 3,944,420 A | * | 3/1976 | Gale et al. | 430/1 |
| 4,049,459 A | * | 9/1977 | Bloom et al. | 430/2 |
| 4,069,049 A | * | 1/1978 | Reich et al. | 430/1 |
| 4,173,474 A | * | 11/1979 | Tanaka et al. | 430/1 |
| 4,367,911 A | * | 1/1983 | Graube | 359/3 |

(Continued)

FOREIGN PATENT DOCUMENTS

EP  0 651 252 A  5/1995

(Continued)

OTHER PUBLICATIONS

Millington, R. B. et al. "A Hologram Biosensor for Proteases" *Sensors and Actuators B*, 1996, pp. 55-59, vol. 33.

*Primary Examiner*—Brian J Sines
(74) *Attorney, Agent, or Firm*—Saliwanchik, Lloyd & Saliwanchik

(57) ABSTRACT

An array of discrete sensors disposed on a substrate, each sensor comprising a holographic support medium and a hologram disposed throughout the volume of the medium, whereby interaction with an analyte results in a variation of a property of the medium.

3 Claims, 2 Drawing Sheets

U.S. PATENT DOCUMENTS

Figure 1:
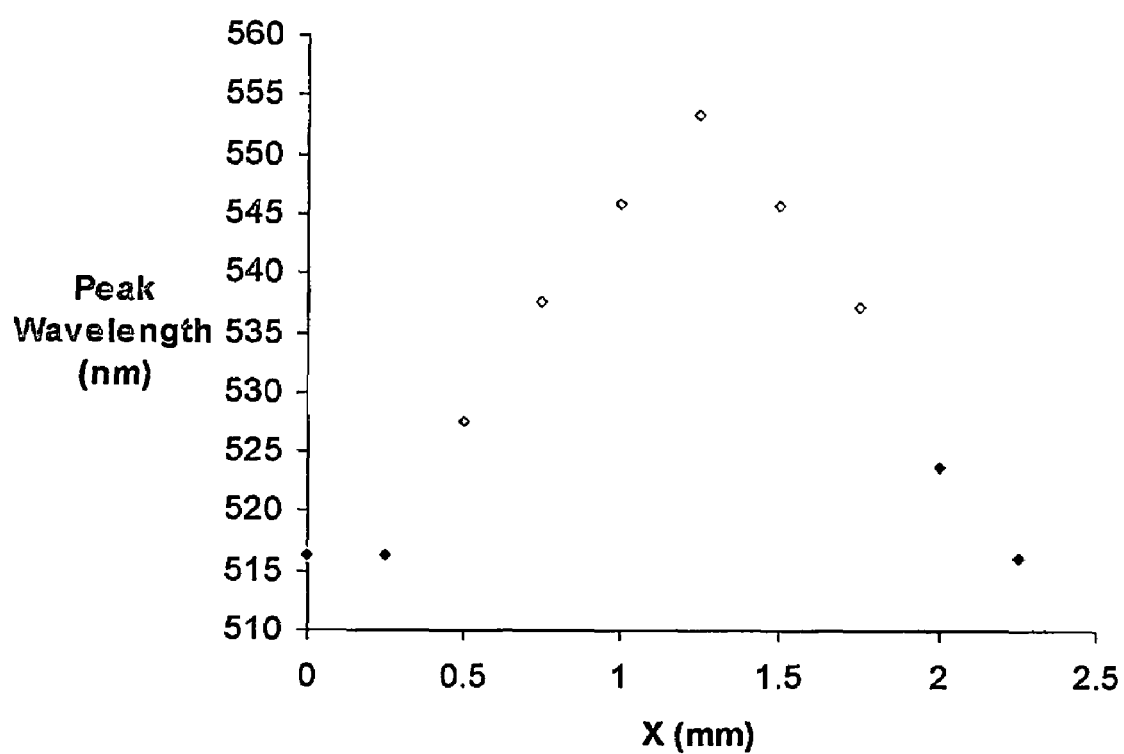

| | | | |
|---|---|---|---|
| 4,856,857 A * | 8/1989 | Takeuchi et al. | 359/3 |
| 4,908,285 A * | 3/1990 | Kushibiki et al. | 430/1 |
| 5,874,187 A * | 2/1999 | Colvin et al. | 430/2 |
| 6,180,288 B1 | 1/2001 | Everhart et al. | |
| 6,436,651 B1 | 8/2002 | Everhart et al. | |
| 6,476,092 B1 * | 11/2002 | Kunita | 522/31 |

FOREIGN PATENT DOCUMENTS

| | | |
|---|---|---|
| WO | WO 95/26499 A | 10/1995 |
| WO | WO 99/63408 A | 12/1999 |
| WO | WO 01/50113 A | 7/2001 |

* cited by examiner

HOLOGRAPHIC SENSORS AND THEIR PRODUCTION

This application is a National Stage Application of International Application No. PCT/GB2004/000979, filed Mar. 11, 2004; which claims priority to Great Britain Application No. 0305591.0, filed Mar. 11, 2003.

FIELD OF THE INVENTION

This invention relates to the production of holographic sensors and arrays of such sensors.

BACKGROUND TO THE INVENTION

WO-A-95/26499 discloses a sensor based on a volume hologram. This sensor comprises an analyte-sensitive matrix having an optical transducing structure disposed throughout its volume. Typically, such a sensor is made of silver halide particles disformed in gelatin. Because of this physical structure, the optical signal generated by the sensor is very sensitive to volume changes or structural rearrangements taking place in the matrix, as a result of interaction or reaction with the analyte.

An alternative method of production of a holographic sensor is disclosed in WO-A-99/63408. A sequential treatment technique is used, wherein the polymer film is made first and sensitive silver halide particles are added subsequently. These particles are introduced by diffusing soluble salts into the polymer matrix where they react to form an insoluble light-sensitive precipitate. The holographic image is then recorded.

SUMMARY OF THE INVENTION

The present invention is based, at least in part, on an application of the ability of the sensors described above to be small, sensitive and analyte-specific. They can therefore be used to provide massively parallel data, when used in an array or pattern. There are many ways in which an array of sensors according to the invention can be produced.

According to one aspect of the invention, an array of sensors is disposed on a substrate, each sensor comprising a holographic support medium and a hologram disposed throughout the volume of the medium, whereby interaction with an analyte results in a variation of a property of the medium. The sensors may have different sensitivities.

Another aspect of the invention is a method for the production of such an array, which comprises the steps of: forming discrete areas of a holographic support medium by screen printing a liquid comprising polymerisable components on a substrate; polymerising the liquid; disposing throughout the medium a holographic recording material; and recording a holographic image. The liquid is preferably polymerised by photopolymerisation.

Another aspect of the invention is a method for the production of a holographic sensor, which comprises the steps of: forming a holographic support medium by the photopolymerisation of a sample of polymerisable components, wherein a region of the sample is in contact with a mask containing oxygen such that polymerisation is inhibited in said region; disposing within the medium a holographic recording material; and recording a holographic image. Such a method may be used to produce an array of sensors.

The invention may allow for the mass-production of well-defined "spot" holographic sensors. Sensors of complex shape or patterning may also be produced. A method of the invention may be facilitated by using a contact printing process to record the holographic image.

DESCRIPTION OF THE PREFERRED EMBODIMENTS

A holographic sensor of the type used in the present invention generally comprises a holographic element which comprises a holographic support medium and a hologram disposed throughout the volume of the medium. The support medium interacts with an analyte resulting in a variation of a physical property of the medium. This variation induces a change in an optical characteristic of the holographic element, such as its polarisability, reflectance, refractance or absorbence. If any change occurs whilst the hologram is being replayed by incident broad band, non-ionising electromagnetic radiation, then a colour, intensity or other change may be observed.

A holographic sensor may be used for detection of a variety of analytes, simply by modifying the composition of the support medium. The medium preferably comprises a polymer matrix, the composition of which is preferably optimised to obtain a high quality film, i.e. a film having a uniform matrix in which holographic fringes can be formed. The polymer matrix is preferably formed by the copolymerisation of acrylamide and/or methacrylate-derived comonomers. In particular, the monomer HEMA (hydroxyethyl methacrylate) is readily polymerisable and cross-linkable. PolyHEMA is a versatile support material since it is swellable, hydrophilic and widely biocompatible.

Other examples of holographic support media are gelatin, K-carageenan, agar, agarose, polyvinyl alcohol (PVA), sol-gels (as broadly classified), hydro-gels (as broadly classified) and acrylates. Gelatin is a standard matrix material for supporting photosensitive species such as silver halide grains. Gelatin can also be photo-cross-linked by Cr(III) ions, between carboxyl groups on gel strands.

The nature of the substrate on which the array is formed is not critical. It may be a sheet or film of any essentially inert polymeric or other material.

These are several methods by which an array of sensors may be formed. In one such method, the surface of the substrate is made reactive (e.g. by silanisation of glass, treating a plastics material with acid or glow discharge, or imine activation of a polyamide, polyolefin or polymethyl methacrylate) in selected areas (e.g. using a mask) and a liquid is applied which then reacts in the activated areas. Alternatively, the liquid is applied only in selected areas, and the discrete areas of the array are defined by masking or treatment of the substrate surface to define relatively wettable and non-wettable areas.

Suitable methods include lithography, screen printing and contact printing. For example, the array may be formed by application of a relatively viscous liquid to define areas of the substrate, by chemical cross-linking in defined areas with subsequent removal of the less (or more) cross-linked material (e.g. following the application of a base hydrogel with areas of different reactivity) or by screen printing of spots of material, with or without photochemical de(protection). It will be appreciated that some of these techniques, particularly screen printing, depend on controlling the viscosity of the applied liquid, and this can be done in various ways. For example, the liquid that is applied comprises a viscosity-increasing additive which may be an inert polymer or a component that can be washed out or otherwise removed from the array. A suitable agent for this purpose is poly(ethylene oxide) (PEO). PEO is also insoluble to oxygen and thus may have the effect of reducing the solubility of oxygen in the polymerisation mixture. This may enhance polymerisation in peripheral regions where oxygen may otherwise inhibit the reaction, producing a more uniform polymer distribution across the holographic element. A holographic element formed using this method may be "brighter" and of greater sensitivity. The presence of PEO may also limit the size of the silver grains, minimising "fogging" of the hologram. An alternative approach is to partially polymerise components of the liquid, e.g. so that they are in oligomeric form, such as 20-50 mars.

Alternatively, a method of the invention may comprise forming the holographic support medium by a photopolymerisation process, in which the shape or patterning of the support medium is defined using a mask which contains oxygen or another inhibitor of free radical polymerisation.

Oxygen reacts with radicals to form peroxy radicals, which have an insufficient reactivity to continue the free radical polymerisation process, leading to chain termination and incomplete polymerisation. In addition, oxygen is highly soluble in a number of materials, including fluoropolymers such as polytetrafluoroethylene (PTFE) and fluorinated ethylene-polypropylene. Thus, oxygen can be dissolved into the mask, which is then applied in contact with the desired region of the polymerisation mixture. Upon polymerisation of the monomer mixture, the support medium is formed up to the point of contact with the mask. The elevated concentration of oxygen in the masked regions prevents radical polymerisation occurring in these areas. This method is a simple, versatile method for producing holographic sensors, allowing control over the shape of the holographic element.

Since a method of the present invention provides sensitivity around the edges of the holographic element, this may be exploited to produce sensors which detect a plurality of properties/analytes simultaneously. A sensor of the invention may comprise a plurality of holographic elements, each element sensitive to a specific analyte. Two such elements may be abutted. A single beam of light can be directed at the abutted edges of the elements and changes in element monitored simultaneously. This approach may be used to produce, for example, a dual pH/alcohol sensor.

The technology described herein may have particular value in the contexts of the technologies described in WO-A-03/087899 and WO-A-04/005922.

The following Examples illustrate the invention.

EXAMPLE 1

An array of 3 mm "spot" holographic sensors was produced using a contact-printing process. A mask comprising fluorinated ethylene-polypropylene polymer (FEP) was used to define the "spot" locations in which HEMA monomers were photopolymerised, to produce the holographic support medium. The high concentration of oxygen dissolved in the fluoropolymer inhibited free radical polymerisation occurring in the masked regions, allowing the holographic "spots" to be developed.

EXAMPLE 2

A polymer was formed from HEMA (200 µl), EDMA (7 µl) and MM (2 µl), dissolved in 2% DMPA in propan-1-ol (200 µl). Polymerisation was conducted by 45 minute exposure time to UV light at 365 nm, slides polymerised with 70 µl titres of polymerisation mixture as is standard.

The slides were then dipped for 60 seconds in an activation mixture (69.5 mg EDC and 38.2 mg NHS, in 1.94 ml ultra-pure water). They were then immediately spotted by pipette with 2 µl droplets of amino-linked DNA (10 base oligonucleotide 133.3 nmol/ml in pure water), briefly dried and then washed with copious water and TE buffer.

Figure 2:
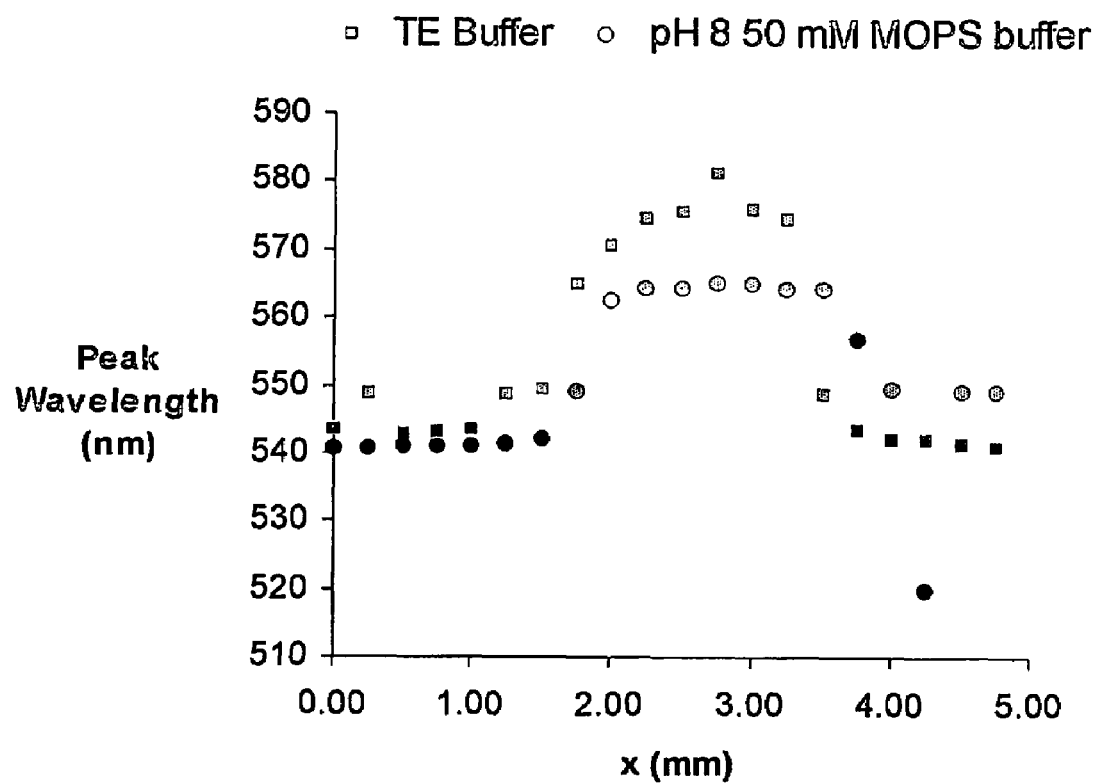

In the resulting array, the spotted regions corresponded to the areas in which DNA was attached. FIGS. 1 and 2 are scanning profiles of a selection of DNA "spots". FIG. 1 shows the x profile of a spot (taken in TE buffer at 30° C.). FIG. 2 shows the x profile of a spot under two different sets of conditions, namely TE buffer at 30° C. and 50 mM MOPS buffer at pH8 and 30° C.

EXAMPLE 3

A holographic sensor was produced by the polymerisation of HEMA monomers in the presence of PEO (7.5% w/v). A silver halide-based recording material was then disposed onto the resulting polymer matrix, and a hologram recorded. A standard polyHEMA holographic sensor was also produced for comparison.

The addition of PEO in the polymerisation mixture had no detrimental effects on the responsiveness of the sensor to pH and alcohol. The presence of PEO also produced a brighter, less "foggy" hologram.

EXAMPLE 4

A dual alcohol/pH sensor was produced by separate polymerisation of HEMA monomers and a HEMA/MAA monomer mixture respectively, each polymerisation mixture containing PEO.

The sensor was then tested for sensitivity to changes in pH and alcohol concentration. The presence of PEO resulted in high sensitivity over the cross-section of each sensor. This allowed a single light spot to be used to monitor changes in the two properties simultaneously. Although the pH-sensing holographic element responded to alcohol, the lack of response of the alcohol-sensing element to pH meant that calibration was straightforward.

The invention claimed is:

1. A method for the production of a holographic sensor, which comprises the steps of: forming a holographic support medium by the photopolymerisation of a sample of polymerisable components, wherein a region of the sample is in contact with a mask containing oxygen such that polymerization is inhibited in said region; disposing within the support medium a holographic recording material; and recording a holographic image.

2. The method according to claim 1, wherein the mask comprises a polymer in which oxygen is dissolved.

3. The method according to claim 2, wherein the polymer contains a fluorinated group.

* * * * *